(12) United States Patent
Kawahara (10) Patent No.: US 11,173,284 B2
(45) Date of Patent: Nov. 16, 2021

(54) MEDICAL GUIDE WIRE

(71) Applicant: GUNZE LIMITED, Kyoto (JP)

(72) Inventor: Makoto Kawahara, Moriyama (JP)

(73) Assignee: GUNZE LIMITED, Kyoto (JP)

( * ) Notice: Subject to any disclaimer, the term of this patent is extended or adjusted under 35 U.S.C. 154(b) by 356 days.

(21) Appl. No.: 15/768,423

(22) PCT Filed: Oct. 27, 2016

(86) PCT No.: PCT/JP2016/081862
§ 371 (c)(1),
(2) Date: Apr. 13, 2018

(87) PCT Pub. No.: WO2017/086114
PCT Pub. Date: May 26, 2017

(65) Prior Publication Data
US 2018/0311476 A1    Nov. 1, 2018

(30) Foreign Application Priority Data

Nov. 17, 2015    (JP) .............................. JP2015-224464

(51) Int. Cl.
*A61M 25/09*    (2006.01)
*A61M 25/00*    (2006.01)

(52) U.S. Cl.
CPC ............ *A61M 25/09* (2013.01); *A61M 25/00* (2013.01); *A61M 2025/09091* (2013.01);
(Continued)

(58) Field of Classification Search
CPC .................. A61M 25/09; A61M 25/00; A61M 2025/09091; A61M 2025/09108;
(Continued)

(56) References Cited

U.S. PATENT DOCUMENTS

| 4,626,240 | A | * | 12/1986 | Edelman | ............. | A61M 5/1582 |
| | | | | | | 604/43 |
| 2009/0181156 | A1 | * | 7/2009 | Nesbitt | ................... | A61L 31/10 |
| | | | | | | 427/2.1 |

(Continued)

FOREIGN PATENT DOCUMENTS

| EP | 2229974 B1 * | 12/2018 | ............ A61M 25/09 |
| JP | 2010-011883 A | 1/2010 | |

(Continued)

OTHER PUBLICATIONS

International Search Report issued in PCT/JP2016/081862; dated Feb. 7, 2017.

*Primary Examiner* — Patrick Fernandes
(74) *Attorney, Agent, or Firm* — Studebaker & Brackett PC (57) ABSTRACT

A medical guide wire with excellent visibility is provided. A medical guide wire including: a wire body (2) that is flexible and long; a covering layer (3) covering a surface of the wire body (2); and a wire material (4) helically arranged on the covering layer (3), wherein the covering layer (3) is formed of a transparent material same as a transparent material of the wire material (4), and the wire material (4) is arranged at a regular pitch along the longitudinal direction of the wire body (2).

6 Claims, 3 Drawing Sheets
(2 of 3 Drawing Sheet(s) Filed in Color)

(52) U.S. Cl.
CPC .............. *A61M 2025/09108* (2013.01); *A61M 2025/09191* (2013.01); *A61M 2205/0222* (2013.01); *A61M 2205/584* (2013.01)

(58) Field of Classification Search
CPC ........... A61M 2025/09191; A61M 2205/0222; A61M 2205/584; A61F 2/958; A61F 2/954; A61B 8/12; A61B 2017/003; A61B 18/1492; A61B 2018/00577; A61L 29/085
See application file for complete search history.

(56) References Cited

U.S. PATENT DOCUMENTS

| | | | |
|---|---|---|---|
| 2009/0306546 A1* | 12/2009 | Knapp | A61B 1/00147 600/585 |
| 2010/0004561 A1* | 1/2010 | Nabeshima | A61M 25/09 600/585 |
| 2011/0071536 A1* | 3/2011 | Kleiner | A61F 2/4601 606/94 |

FOREIGN PATENT DOCUMENTS

| | | |
|---|---|---|
| JP | 2012-070979 A | 4/2012 |
| JP | 2015-181723 A | 10/2015 |
| WO | 2009/090963 A1 | 7/2009 |

\* cited by examiner

MEDICAL GUIDE WIRE

TECHNICAL FIELD

The present invention relates to a medical guide wire.

BACKGROUND ART

Conventionally, a medical guide wire have been used for safely and reliably inserting a catheter into the gastrointestinal system such as the stomach, the small intestine, the large intestine, the liver, and the bile duct. Such a medical guide wire is inserted into the gastrointestinal tract, the bile duct or the like in a state in which the distal end of the medical guide wire is projected from the distal end of the catheter, is moved forward within the gastrointestinal tract, the bile duct or the like by the rotation and pushing or pulling of a hand grip part outside a body, and is inserted to the area near the target site together with the catheter. Here, such an operation is performed with the medical guide wire being viewed through endoscope images to confirm the position and movement of the medical guide wire.

As such a medical guide wire, for example, a medical guide wire has been known, which has visible markers such as a plurality of stripes constituted in combination of different colors on the surface of the wire body to easily confirm the position of the medical guide wire during the exchange of treatment tools or endoscopic therapy.

SUMMARY OF THE INVENTION

Problems to be Solved by the Invention

Though a conventionally known medical guide wire has visible markers such as stripes on its surface as described above, and has a certain effect on visibility through endoscope images, the medical guide wire has a problem that light is unnecessarily reflected on its surface and endoscope images of the surface of the medical guide wire become white in a wide area and difficult to see due to the light emitted from the distal end of the endoscope (halation). Thus, further improvement of visibility is desired.

To solve such a problem, an object of the present invention is to provide a medical guide wire with excellent visibility.

Means for Solving the Problems

The object of the present invention is achieved by a medical guide wire including a wire body that is flexible and long, a covering layer covering a surface of the wire body, and a wire material helically arranged on the covering layer, wherein the covering layer is formed of a transparent material same as a transparent material of the wire material, and the wire material is arranged at a regular pitch along the longitudinal direction of the wire body.

In this medical guide wire, it is preferred that the wire body include a core material and a coloring layer coloring a surface of the core material, and the coloring layer have at least one color of black, white, yellow, blue, red, and green.

It is preferred that an outermost layer composed of the wire material and the covering layer have a maximum value of glossiness in an incident angle range of 30° or more and 80° or less.

It is preferred that the outermost layer have a maximum value of glossiness of 15 or less.

It is preferred that the outermost layer have a difference between the maximum value and the minimum value of glossiness of 1 or more.

Effects of the Invention

According to the present invention, a medical guide wire with excellent visibility can be provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

EMBODIMENTS OF THE INVENTION

Figure 1:
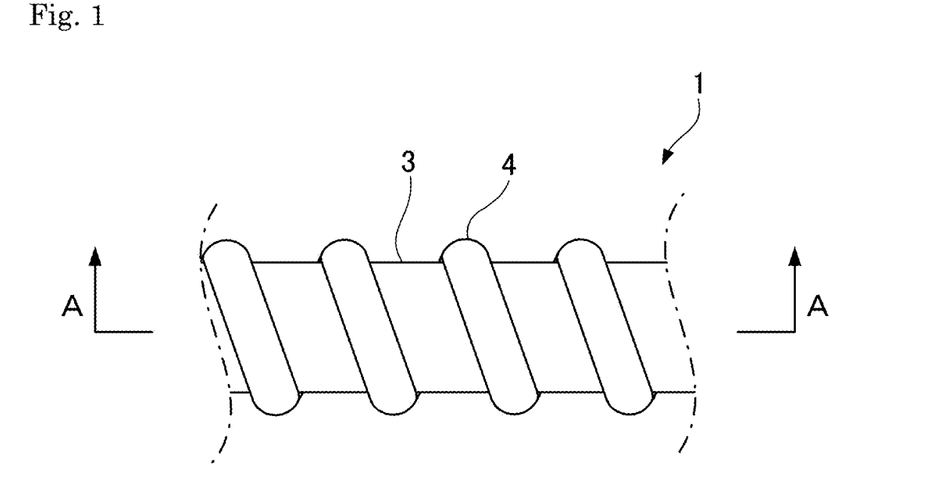
FIG. 1 is an enlarged side view showing an outline configuration of a main part of a distal end part of a medical guide wire according to one embodiment of the present invention.
Figure 2:
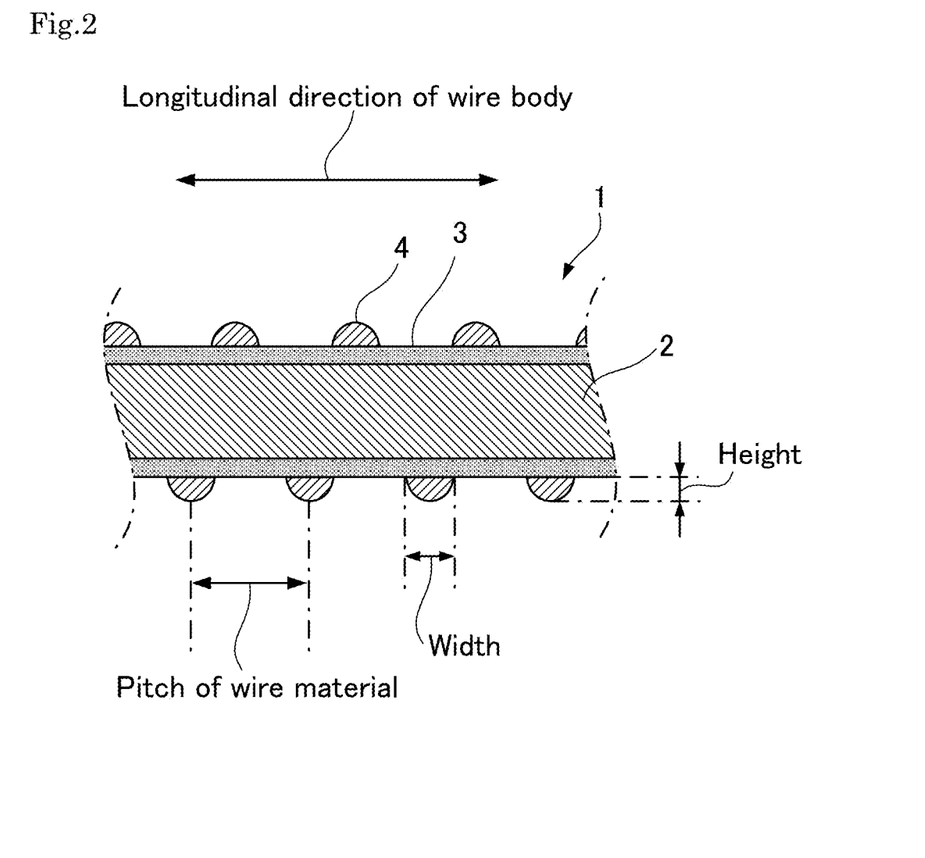
FIG. 2 is an A-A sectional view of FIG. 1.

A medical guide wire 1 according to an embodiment of the present invention is described below with reference to the accompanying drawings. The drawings are partially enlarged or reduced to facilitate the understanding of structure. FIG. 1 is an enlarged side view showing an outline configuration of a main part of the medical guide wire 1 according to one embodiment of the present invention, and FIG. 2 is an A-A sectional view of FIG. 1. The medical guide wire 1 according to the present invention is, for example, a medical guide wire that is used in the state of being into a catheter, and includes a wire body 2, a covering layer 3, and a wire material 4 helically wound and arranged on the covering layer 3, as shown in FIGS. 1 and 2.

The wire body 2 is a long component with flexibility. This wire body 2 can be made of various conventional materials used as a core material of a medical guide wire. For example, the wire body 2 can be made of stainless steel (for example, all kinds of SUS such as SUS304, SUS303, SUS316, SUS316L, SUS316J1, SUS316J1L, SUS405, SUS430, SUS434, SUS444, SUS429, SUS430F, and SUS302). When stainless steel is used as a material of the wire body 2, the medical guide wire 1 can have more excellent pushability and torque transmission.

As a material of the wire body 2, pseudoelastic alloys (including a super-elastic alloy) can also be used. In particular, when the wire body 2 is made of a super-elastic alloy, the medical guide wire 1 can have sufficient overall pliability and resiliency in bending and improved followability to the gastrointestinal tract or bile duct complicatedly curved and bent, resulting in more excellent operativity. Further, the resiliency of the wire body 2 prevents the wire body 2 from acquiring a tendency to bend even after repeated winding and curving of the wire body 2, and thus can prevent the reduction of operativity caused by the bending tendency of the wire body 2 acquired during the use of the medical guide wire 1.

The pseudoelastic alloys include any alloys that are significantly deformed by stress and recover almost to their original shapes on the elimination of the stress, irrespective of the shapes of a stress-strain curve in tension and whether obvious transformation points such as As, Af, Ms, and Mf can be measured or not.

Examples of the preferred composition of the superelastic alloy include Ni—Ti alloys such as an Ni—Ti alloy having 49 to 52% by atom of Ni, Cu—Zn alloys having 38.5 to 41.5% by weight of Zn, Cu—Zn—X alloys having 1 to 10% by weight of X (X is at least one of Be, Si, Sn, Al, and Ga), and Ni—Al alloys having 36 to 38% by atom of Al. Among these, the most preferred alloy is the Ni—Ti alloy.

As a material of the wire body 2, a cobalt alloy can also be used. When the wire body 2 is made of a cobalt alloy, the medical guide wire 1 has especially excellent torque transmission, and problems such as buckling hardly occur. Though the cobalt alloy may be any cobalt alloys containing Co as a constituent element, a cobalt alloy containing Co as a main component (Co base alloy: an alloy in which the content of Co based on the weight ratio is the highest among the elements that constitute the alloy) is preferred, and a Co—Ni—Cr alloy is more preferably used. Using alloys having such compositions makes the above effects more significant. Though the alloys having such compositions have a high elastic modulus and a high elastic limit, they can be cold-formed. The high elastic limit enables the diameter reduction with sufficiently preventing the occurrence of buckling, and thus provides sufficient pliability and rigidity for insertion into a target site.

The wire body 2 may be made of the above materials, or may be composed, for example, of a piano wire.

The wire body 2 may be in various forms. For example, the wire body 2 may be formed of one steel material, or may be formed by interfolding one linear steel material and then twisting it. The wire body 2 may be formed by twisting a plurality of linear steel materials, or may be formed by twisting a linear steel material and a linear resin member. Further, the wire body 2 can have various structures such as a structure in which the center portion is formed of a material different from the material of the surface portion, that is, a two-layer structure, for example, a member obtained by coating the outer surface of the center portion made of a metal with thermosetting resin. The full-length of the wire body 2 is, without particular limitation, preferably about 2000 to 5000 mm.

The wire body 2 may be formed so that the outside diameter is almost constant or may be formed in a tapered form in which the outer diameter in the distal end part is reduced toward the tip. When the distal end part of the wire body 2 is formed in a tapered form in which the outer diameter is reduced toward the tip, the rigidity (bending rigidity and twist rigidity) of the wire body 2 can be gradually reduced toward the tip. As a result, the distal end part of the medical guide wire 1 can have good passability in narrow parts and pliability, and the medical guide wire has improved followability to the gastrointestinal tract or the bile duct and safety with preventing bending.

The wire body 2 may be formed by connecting a first wire body 2 that constitutes the distal end part and a second wire body 2 part that constitutes the intermediate part and the hand grip part by welding or the like. When the wire body 2 is formed of the first wire body 2 and the second wire body 2, the diameter of the first wire body 2 is preferably designed to be smaller than that of the second wire body 2. The connected part is preferably formed in a tapered form enabling the smooth connection between the first wire body 2 and the second wire body 2. The rigidity (bending rigidity and twist rigidity) of the wire body 2 thus formed can also be gradually reduced toward the tip. As a result, the distal end part of the medical guide wire 1 has good passability in narrow parts and pliability, and the medical guide wire has improved followability to the gastrointestinal tract or the bile duct and safety with preventing bending.

The wire body 2 may be formed to include a core material formed of the above materials and a coloring layer coloring a surface of the core material. The coloring layer is provided for recognizing the movement of the medical guide wire 1 along the axial direction, and is preferably formed to have at least one color of black, white, yellow, blue, red, and green. In particular, the coloring layer is preferably formed to have a plurality of stripes in combination of different colors. As a method for forming such a coloring layer, for example, without particular limitation, there has been known a method of attaching a colored hollow tube to the core material by thermally shrinking the colored hollow tube inside which the core material is placed to wrap the core material.

The covering layer 3 is formed to cover the surface of the wire body 2, and is formed of a transparent material. Though the transparent material that constitutes the covering layer 3 is preferably a transparent material containing no coloring agent, a light-transmissive colored transparent material can also be used.

The method for forming the covering layer 3 by covering the surface of the wire body 2 with the transparent material is not specifically limited, and various methods can be used. Examples of the method include a coating method in which the wire body 2 is dipped in a solution prepared with a transparent resin material and an appropriate solvent and then dried, and a method in which a tube body prepared with a transparent resin material inside which the wire body 2 is placed is thermally shrunk to cover the wire body 2. The thickness of the covering layer 3 formed on the surface of the wire body 2 is normally 1 µm to 50 µm, preferably 3 µm to 30 µm, particularly preferably 5 µm to 20 µm in dry thickness.

The wire material 4 helically wound and arranged on the covering layer 3 is wound and arranged at a regular pitch along the longitudinal direction of the wire body 2. The wire material 4 is formed of a material same as the transparent material forming the covering layer 3. The wire material 4 is formed to have an almost constant thickness along the longitudinal direction before it is wound on the covering layer 3, and the maximum diameter is, for example, 10 µm to 200 µm, preferably 15 µm to 150 µm, particularly preferably 30 µm to 100 µm. Here, the pitch means, as shown in the sectional view of FIG. 2, the center-to-center distance between the parts of the wire material 4 neighboring along the longitudinal direction of the wire body 2. In the present invention, the wire material 4 is helically wound so that the center-to-center distances (pitches) between the parts of the wire material 4 are equal. The center-to-center distance (pitch) between the parts of the wire material 4 can be any length, and is, for example, 15 µm to 5000 µm, preferably 30 µm to 1000 µm, particularly preferably 50 µm to 700 µm.

Here, the light transmission of the transparent material that constitutes the covering layer 3 and the wire material 4 at a wavelength of 600 to 750 nm is preferably 50% or more, and is more preferably 70% or more. Though the light transmission is preferably directly measured with a microspectrophotometer using the covering layer 3 or the wire material 4 arranged on the wire body 2, a film having a composition same as the composition of the covering layer 3 and the wire material 4 to be measured may be alternatively used when such a direct measurement is difficult. In such a case, the film thickness is preferably 30 μm. With such a thickness, the difference between the value in the direct measurement and the value in the film measurement will be 5% or less. The transparent material that constitutes the covering layer 3 and the wire material 4 is, preferably, for example, a fluororesin material with lubricity. Examples of the fluororesin material include tetrafluoroethylene-perfluoroalkylvinyl ether copolymer (PFA, melting point of 300 to 310° C.), polytetrafluoroethylene (PTFE, melting point of 330° C.), tetrafluoroethylene-hexafluoropropylene copolymer (FEP, melting point of 250 to 280° C.), ethylene-tetrafluoroethylene copolymer (ETFE, melting point of 260 to 270° C.), polyvinylidene fluoride (PVDF, melting point of 160 to 180° C.), polychlorotrifluoroethylene (PCTFE, melting point of 210° C.), tetrafluoroethylene-hexafluoropropylene-perfluoroalkylvinyl ether copolymer (EPE, melting point of 290 to 300° C.), and a fluororesin material such as a copolymer containing these polymers. Among them, PFA, PTFE, FEP, ETFE, and PVDF have excellent sliding properties and thus are preferred. As the material that constitutes the covering layer 3 and the wire material 4, hydrophilic resin materials such as polyvinyl alcohol, polyvinylpyrrolidone, a polyethylene oxide macromolecular substance, a maleic anhydride macromolecular substance, an acrylamide macromolecular substance, and water soluble nylon can also be used.

The method for manufacturing the wire material 4 is not specifically limited and, for example, conventionally known methods such as a method of spinning a resin material same as the transparent resin material that constitutes the covering layer 3 into a thread by extrusion can be used. The method for winding the wire material 4 on the covering layer 3 is not specifically limited, and includes, for example, a winding method in which a covering instrument used to manufacture a covering thread is used.

The wire material 4 helically wound and arranged on the covering layer 3 is entirely thermally fused and integrated with the covering layer 3. The sectional shape of the wire material 4 thus thermally fused is preferably a semi-cylindrical lens shape or a planoconvex lens shape (English capital letter "D" shape), as shown in the sectional view of FIG. 2. The value of "height/width" for the sectional shape such as the semi-cylindrical lens shape is preferably 5% or more, more preferably 10% or more, and, in particular, further more preferably 15% or more. The value of "height/width" is preferably 60% or less, more preferably 50% or less, and, in particular, further more preferably 40% or less.

Examples of the method for thermally fusing the wire material 4 onto the covering layer 3 include a method in which the wire material 4 is helically wound onto the outer surface of the covering layer 3 and then thermally fused to the surface of the covering layer 3 by heating and melting the wire material 4 and the covering layer 3. The heating can be performed, for example, by heating the outside of the wire material 4 wound on the covering layer 3 on the wire body 2 using a chamber type heat treatment instrument.

When the wire body 2 is formed of, for example, a metallic material easily conducts electricity, the wire material 4 and the covering layer 3 can be bonded together by energizing both the ends of the wire body 2 to heat the wire body 2, and melting the covering layer 3 that covers the surface of the wire body 2 with the heat.

In particular, when the wire body 2 is formed of a conducting material (a material that easily conducts electricity) and the covering layer 3 is formed of a material less magnetic than the wire body 2, the wire material 4 can be bonded onto the outer surface of the covering layer 3 by heating the wire body 2 from the outside of the wire material 4 arranged on the covering layer 3 by electromagnetic induction using an electromagnetic induction heating machine to melt the covering layer 3 with the heat of the heated wire body 2, and fusing the wire material 4 onto the covering layer 3. The material less magnetic than the wire body 2 means, in addition to a material more weakly magnetic than the wire body 2, a nonmagnetic material. The electromagnetic induction heating is a heating method used for an electromagnetic cooker (an IH cooking heater), high-frequency welding and the like. This method utilizes a principle in which an alternating current applied to a coil changes a magnetic field (magnetic flux density), and generates an induction current (eddy current) in a conductive substance placed in the magnetic field, and the resulting resistance causes the conductive substance itself to generate heat.

The density of the induction current generated in the wire body 2 heated by electromagnetic induction increases from the center toward the surface of the wire body 2. Thus, the surface of the wire body 2 is heated more quickly (intensively) than its inside, allowing the efficient melting of the covering layer 3. When the frequency of the current flowing in the electromagnetic induction heating machine (the alternating current flowing in a coil) is set high, a site at the surface of the wire body 2 intensively generates heat, and when the frequency of the current is set low, the inside of the wire body 2 also evenly generates heat. Thus, it is preferred that the frequency of the current flowing in the electromagnetic induction heating machine can be changed as needed.

As described above, when the wire body 2 is electrically heated or heated by electromagnetic induction to soften or melt mainly the covering layer 3 covering the surface of the wire body 2, and form thermally fused parts to bond the wire body 2 and the covering layer 3 together, the thermal effect on the wire material 4 will be decreased. As a result, the molecular orientation contributing to the physical property of the wire material 4 tends to be maintained, and the mechanical strength of the wire material 4 can be kept higher. Unlike the heating by heat transfer or radiation and energy line emission or the like from the outside, softening or melting mainly the covering layer 3 can inhibit the softening and resulting significant deformation in the vicinity of the top of the wire material 4 that constitutes the surface protrusions in the outer surface of the medical guide wire 1, and achieve good visibility with maintaining the sliding properties of the medical guide wire 1 based on the surface protrusions (the wire material 4).

As described above, the medical guide wire 1 according to the embodiment have a structure in which the wire material 4 and the covering layer 3 that constitute the outermost layer are formed of the same transparent material, and the wire material 4 is wound and arranged on the covering layer 3 at a regular pitch (a regular interval). When the medical guide wire 1 having such a structure and an endoscope are inserted into a catheter, and the medical guide wire 1 is viewed with the light from the endoscope emitted to the medical guide wire 1 inside the catheter, a part of the light emitted to the wire material 4 is reflected to the camera lens side of the endoscope, and a part of the wire material 4 is viewed in the state of shining in dots or linearly and excessive reflection of light is inhibited. Thus, the medical guide wire 1 has excellent visibility, and an endoscope observer can correctly recognize the position of the medical guide wire 1 inside the catheter. When the medical guide wire 1 is moved inside the catheter, strength of shining (strength of reflection) changes in response to the movement, and the medical guide wire 1 is viewed as if a part of the surface of the guide wire is blinking. Thus, the endoscope observer can easily recognize the movement of the medical guide wire 1 inside the catheter, and correctly recognize the position and movement state of the medical guide wire 1.

As shown in FIG. 2, a transparent wire material 4 whose sectional shape is a semi-cylindrical lens shape or a plano-convex lens shape (English capital letter "D" shape) is helically arranged on the covering layer 3, and thus, the wire material 4 acts like semi-cylindrical prism, and the emitted light is easily reflected at the plane side (the side of interface with the covering layer 3). Such a feature allows the endoscope observer to easily recognize the pattern under the wire material 4 (the coloring layer), for example, when a coloring layer such as stripes is formed on the surface of the wire body 2, and thus the medical guide wire 1 according to the present invention has extremely excellent visibility in combination with the above effect of the inhibition of excessive reflection of light and the view of a part of the wire material 4 shining in dots or linearly.

The inventors of the present invention prepared a sample of a conventionally used medical guide wire (Sample 1) and samples of the medical guide wire 1 according to the present invention (Samples 2 to 10), and measured their glossiness to confirm the above effects as below. A wire body 2 having an Ni—Ti alloy with a diameter of 0.5 mm as the core material and a black coloring layer on the surface of the core material was used for each sample. The covering layer 3 for covering the surface of the wire body 2 of each sample was formed of tetrafluoroethylene-perfluoroalkylvinyl ether copolymer (PFA). The thickness of the covering layer 3 was 10 μm. The sectional shape and pitch of the wire material 4 helically arranged on the covering layer 3 was different among the samples, as shown in Table 1. The details of the sectional shape of the wire material 4 helically arranged on the covering layer 3 were as follows: "Height" and "Width" shown in FIG. 2 of Samples 2 to 4 were 15 μm and 100 μm, respectively; "Height" and "Width" in FIG. 2 of Samples 5 to 7 were 28 μm and 170 μm, respectively; and "Height" and "Width" of Samples 8 to 10 were 40 μm and 250 μm, respectively. The diameter of each wire material 4 before helically arranged on the covering layer 3 was as follows: the diameters of Samples 2 to 4 were 40 μm; the diameters of Samples 5 to 7 were 70 μm; and the diameters of Samples 8 to 10 were 100 μm. Each wire material 4 was formed of the material same as the material of the covering layer 3 (PFA). The outermost layer of Sample 1 was formed of the covering layer 3 only, without the wire material 4 wound and arranged on the covering layer 3. The wire material 4 and the covering layer 3 were thermally fused and fixed together, and the thermal fusion conditions were far-infrared heating.

The glossiness was measured at incident angle/acceptance angle of 20°/20°, 45°/45°, 60°/60°, 75°/75°, and 85°/85° with respect to the axial direction (longitudinal direction) of each sample of the medical guide wire and according to JISZ8741 for other conditions using Gloss MeterVG7000 (manufactured by NIPPON DENSHOKU INDUSTRIES CO., LTD.). The measurement results of the glossiness of the samples are shown in Table 1. The differences between the maximum value and the minimum value of the glossiness (MAX−MIN) are also shown in Table 1.

TABLE 1

| | Height (μm) | Width (μm) | Pitch (μm) | Glossiness | | | | | MAX − MIN |
|---|---|---|---|---|---|---|---|---|---|
| | | | | 20° | 45° | 60° | 75° | 85° | |
| Sample 1 | — | — | — | 1.5 | 6.0 | 7.4 | 19.8 | 35.0 | 33.5 |
| Sample 2 | 15 | 100 | 300 | 1.0 | 4.3 | 5.2 | 9.7 | 1.2 | 8.7 |
| Sample 3 | 15 | 100 | 500 | 1.3 | 5.1 | 6.1 | 12.9 | 3.8 | 11.6 |
| Sample 4 | 15 | 100 | 700 | 1.4 | 5.4 | 6.4 | 14.3 | 9.4 | 12.9 |
| Sample 5 | 28 | 170 | 300 | 0.8 | 2.7 | 2.3 | 1.4 | 0.6 | 2.1 |
| Sample 6 | 28 | 170 | 500 | 1.0 | 3.7 | 4.0 | 5.7 | 1.3 | 4.7 |
| Sample 7 | 28 | 170 | 700 | 1.0 | 4.0 | 4.7 | 8.5 | 1.4 | 7.5 |
| Sample 8 | 40 | 250 | 300 | 0.4 | 1.4 | 0.7 | 1.3 | 0.9 | 1.0 |
| Sample 9 | 40 | 250 | 500 | 0.7 | 2.5 | 2.5 | 1.6 | 0.8 | 1.8 |
| Sample 10 | 40 | 250 | 700 | 0.9 | 3.2 | 3.4 | 5.1 | 1.3 | 4.2 |

The measurement results of the glossiness of Samples 1 to 10 show that in Sample 1, which had no wire material 4 wound and arranged in a predetermined interval (a predetermined pitch) on the covering layer 3, the glossiness increased as the incident angle of the light increased and the glossiness would be max at an incident angle of 90°, and Samples 2 to 10 (the samples of the medical guide wire according to the present invention), which each had the wire material 4 wound and arranged in a predetermined interval (a predetermined pitch) on the covering layer 3, each had a maximum value at an incident angle lower than 90°. More specifically, Samples 2 to 4, Samples 6 to 7, and Sample 10 had their maximum values of glossiness at an incident angle around 75°, and Sample 5 and Samples 8 to 9 had their maximum values of glossiness at an incident angle around 45°. These results show that the outermost layer formed of the wire material 4 and the covering layer 3 of the medical guide wire according to the present invention has a maximum value of the glossiness in an incident angle range of 30° or more and 80° or less.

Figure 3:
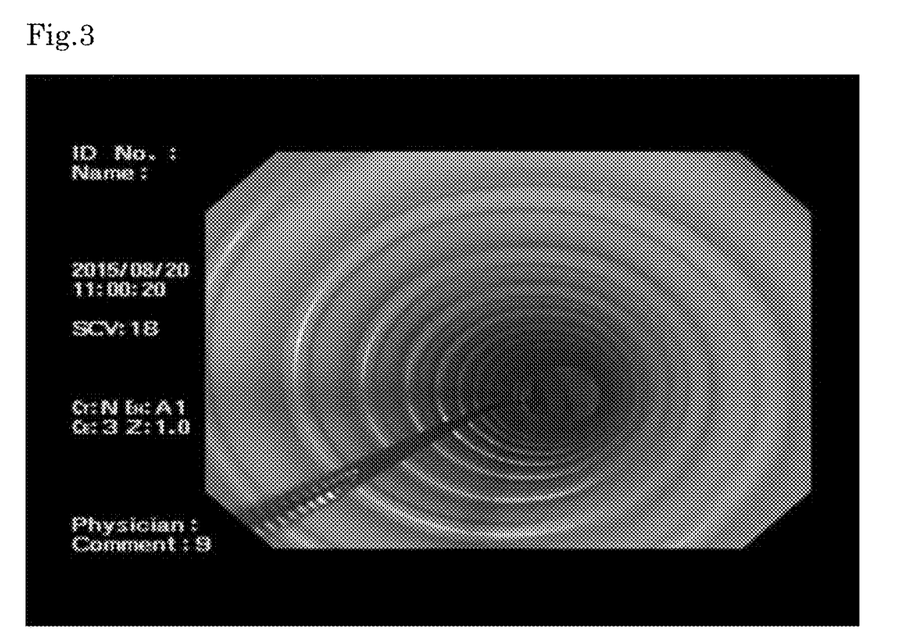
FIG. 3 is an endoscope image of a medical guide wire according to the present invention (Sample 5 in Table 1) inserted into a catheter.
Figure 4:
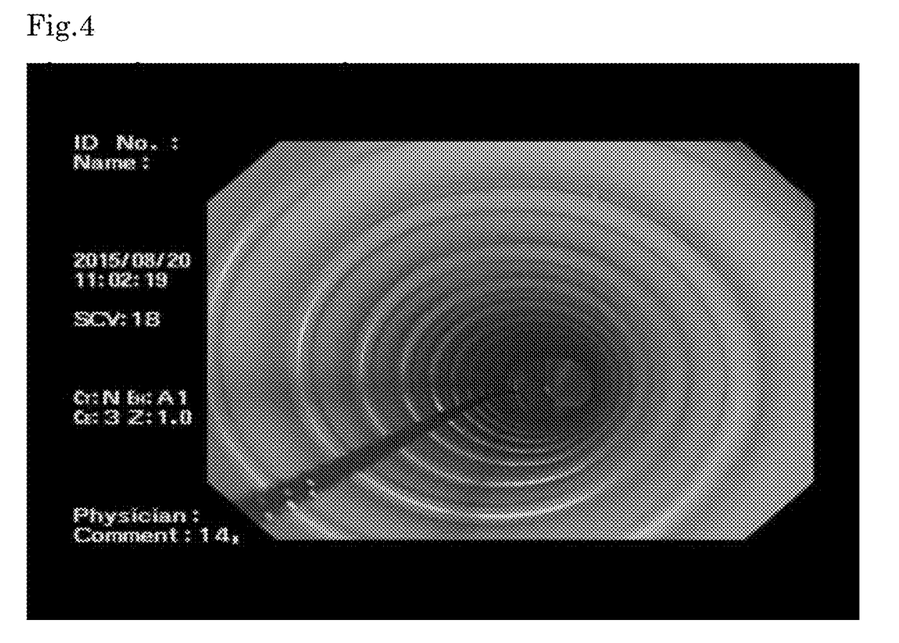
FIG. 4 is an endoscope image of a medical guide wire according to the present invention (Sample 10 in Table 1) inserted into a catheter.
Figure 5:
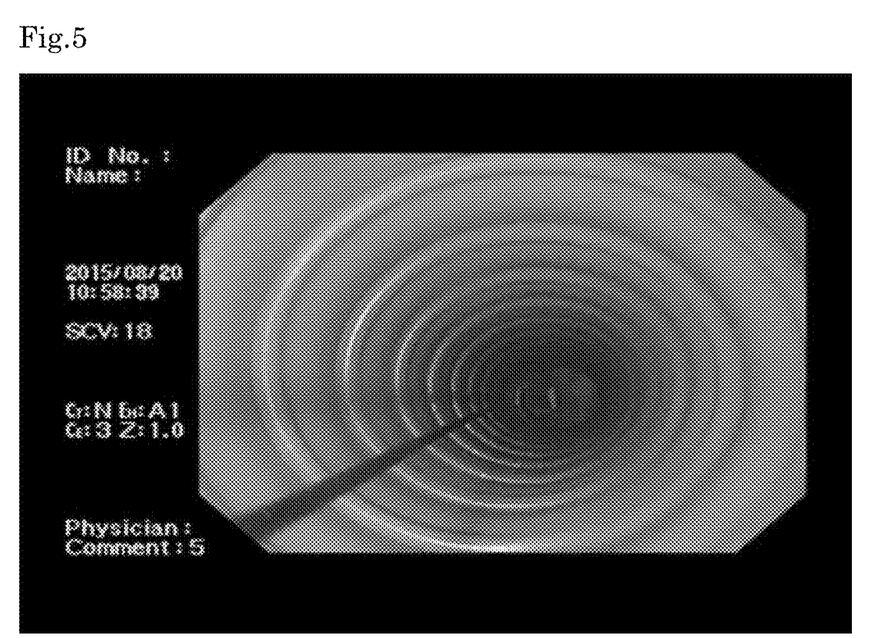
FIG. 5 is an endoscope image of a conventional medical guide wire (Sample 1 in Table 1) inserted into a catheter.

When the medical guide wire inserted into a catheter is viewed using the endoscope inside the catheter, the guide wire area ahead of the camera lens is viewed though the camera lens provided in the endoscope distal end, and the light from the endoscope is emitted from the light source provided in the endoscope distal end. As described above, the outermost layer (the layer formed of the covering layer 3 and the wire material 4) of the medical guide wire 1 according to the present invention has a maximum value of the glossiness in an incident angle range of 30° or more and 80° or less, and thus, as shown in the endoscope images of FIGS. 3 and 4, the points that shine most (the maximum bright points) are necessarily ahead of the endoscope distal ends. Therefore, an endoscope observer can correctly recognize the position or movement state of the medical guide wire 1 based on the maximum bright points, the shining points formed at a certain interval before and after the maximum bright points, or the change of the shining points (the change viewed as blinking). Here, FIG. 3 is an endoscope image of Sample 5 inserted into a catheter, and FIG. 4 is an endoscope image of Sample 10 inserted into a catheter. In FIGS. 3 and 4, a plurality of white points lined in a certain interval in the frontward part of the medical guide wire 1 (lower left of the image) are the shining points reflecting the light from the endoscope. In contrast, the outermost layer of the medical guide wire according to Sample 1, which is a conventional sample, has a maximum value of the glossiness at an incident angle around 90°, and thus the maximum bright point is not formed ahead of the endoscope distal end. In addition, as shown in the endoscope image of FIG. 5, shining points cannot be formed before and after the maximum bright point due to the lack of the wound and arranged wire material 4, and thus, Sample 1 has insufficient visibility.

The maximum value of the glossiness of the conventional Sample 1 was 35, and those of Samples 2 to 10 according to the present invention were 15 or less, showing a significant reduction effect on the maximum values of the glossiness. Thus, because the maximum value of the glossiness of the outermost layer of the medical guide wire 1 is 15 or less, the excessive reflection of light is inhibited, and extensive halation does not occur, resulting in the improved visibility of the medical guide wire from the endoscope observer. When the surface of the wire body 2 has the coloring layer having visible markers such as a plurality of stripes in combination of different colors, the coloring layer can be more easily viewed, and thus the endoscope observer can correctly recognize the position and the movement state of the medical guide wire inside the catheter.

The differences between the maximum value and the minimum value of the glossiness (MAX−MIN) of Samples 2 to 10 according to the present invention were 50% or less of that of the conventional Sample 1, and thus it is understood that Samples 2 to 10 according to the present invention have smaller differences between the maximum value and the minimum value of the glossiness. This also shows that the medical guide wire 1 according to the present invention inhibits the excessive reflection of light and improves the visibility of the medical guide wire 1 from the endoscope observer. Because the differences between the maximum value and the minimum value of the glossiness of the outermost layers of the Samples 2 to 10 are 1.0 or more, garish glossiness can be formed in the light emitted area, and thus the endoscope observer can easily view the medical guide wire inside the catheter.

In Sample 2 to Sample 10, when the pitches of the wire materials 4 helically arranged on the covering layers 3 are the same, the maximum value of the glossiness decreased as the diameter of the wire material 4 wound and arranged increased (for example, for the pitch of 300 μm, the maximum value of the glossiness decreased in the order of Sample 2 (the wire material diameter: 40 μm), Sample 5 (the wire material diameter: 70 μm), and Sample 8 (the wire material diameter: 100 μm)). Therefore, a larger diameter of the wire material 4 wound and arranged on the covering layer 3 is thought to have a higher reduction effect on the glossiness and provide good visibility in the light-emitted endoscope image. In particular, when the wire material diameter is 70 μm or more, a significant reduction effect on the glossiness can be obtained.

The shorter pitch of the wire material 4 wound and arranged on the covering layer 3 has a smaller maximum value of the glossiness, showing that a smaller pitch of the wire material 4 wound and arranged on the covering layer 3 has a higher reduction effect on the glossiness and may provide good visibility in the light-emitted endoscope image.

While the medical guide wire 1 according to the present invention has been described above, the specific configuration is not limited to the above embodiments. For example, though, in the above embodiments, one wire material 4 is helically wound and arranged on the covering layer 3 covering the surface of the wire body 2, as shown in FIGS. 1 and 2, a plurality of the wire materials 4 having different diameter can be helically (double helically) wound on the covering layer 3. In such a configuration, the points that shine most by the light from an endoscope can be formed in different positions on the wire materials 4 having different thicknesses, improving the visibility of the medical guide wire from the endoscope observer.

DESCRIPTION OF REFERENCE SIGNS 1 medical guide wire
2 wire body
3 covering layer
4 wire material

The invention claimed is:
1. A medical guide wire comprising:
a wire body that is flexible and long;
a covering layer covering a surface of the wire body; and
a wire material helically arranged on the covering layer,
wherein the covering layer is formed of a transparent material same as a transparent material of the wire material, the transparent material of the covering layer and the wire material containing no coloring agent, and
the wire material is arranged at a regular pitch along a longitudinal direction of the wire body.
2. The medical guide wire according to claim 1, wherein the wire body includes a core material and a coloring layer coloring a surface of the core material, and
the coloring layer has at least one color of black, white, yellow, blue, red, and green.
3. A medical guide wire comprising:
a wire body that is flexible and long;
a covering layer covering a surface of the wire body; and
a wire material helically arranged on the covering layer,
wherein the covering layer is formed of a transparent material same as a transparent material of the wire material, the transparent material of the covering layer and the wire material containing no coloring agent, and
the wire material is arranged at a regular pitch along a longitudinal direction of the wire body,
wherein an outermost layer composed of the wire material and the covering layer has a maximum value of glossiness in an incident angle range of 30° or more and 80° or less.
4. The medical guide wire according to claim 3, wherein the outermost layer has a maximum value of glossiness of 15 or less.
5. The medical guide wire according to claim 3, wherein the outermost layer has a difference between the maximum value and a minimum value of glossiness of 1 or more.
6. A medical guide wire comprising:
a wire body that is flexible and long;
a covering layer covering a surface of the wire body; and
a wire material helically arranged on the covering layer,
wherein the covering layer and the wire material are formed of a transparent material containing no coloring agent, the wire material is arranged at a regular pitch along a longitudinal direction of the wire body, and the transparent material is one fluororesin material selected from the group consisting of tetrafluoroethylene-perfluoroalkylvinyl ether copolymer (PFA), polytetrafluoroethylene (PTFE), tetrafluoroethylene-hexafluoropropylene copolymer (FEP), ethylene-tetrafluoroethylene copolymer (ETFE), polyvinylidene fluoride (PVDF), polychlorotrifluoroethylene (PCTFE), tetrafluoroethylene-hexafluoropropylene-perfluoroalkylvinyl ether copolymer (EPE), and a copolymer containing PFA, PTFE, FEP, ETFE, PVDF, PCTFE, and/or EPE, or one hydrophilic resin material selected from the group consisting of polyvinyl alcohol, polyvinylpyrrolidone, a polyethylene oxide macromolecular substance, a maleic anhydride macromolecular substance, an acrylamide macromolecular substance, and water soluble nylon, and the covering layer and the wire material have a same material composition.

* * * * *